(12) United States Patent
Campbell et al.

(10) Patent No.: US 6,309,383 B1
(45) Date of Patent: Oct. 30, 2001

(54) STENT CRIMPER APPARATUS WITH RADIATION SHIED

(75) Inventors: Thomas H. Campbell, Brentwood; Todd H. Turnlund, Sunnyvale; Robert T. Chang, Belmont, all of CA (US)

(73) Assignee: IsoStent, Inc., Belmont, CA (US)

( * ) Notice: Subject to any disclaimer, the term of this patent is extended or adjusted under 35 U.S.C. 154(b) by 0 days.

(21) Appl. No.: 09/488,187

(22) Filed: Jan. 20, 2000

(51) Int. Cl.[7] .................................................. A61B 17/00
(52) U.S. Cl. ................................ 606/1; 606/108; 606/198
(58) Field of Search ...................................... 606/108, 198, 606/1

(56) References Cited

U.S. PATENT DOCUMENTS

| | | | |
|---|---|---|---|
| 5,836,952 | * 11/1998 | Davis et al. | 606/108 |
| 5,893,852 | * 4/1999 | Morales | 606/108 |
| 6,051,002 | * 4/2000 | Morales | 606/108 |
| 6,074,381 | * 6/2000 | Dinh et al. | 606/1 |

* cited by examiner

*Primary Examiner*—Linda C. M. Dvorak
*Assistant Examiner*—Jocelyn D Ram (74) *Attorney, Agent, or Firm*—Beyer Weaver & Thomas LLP (57) ABSTRACT

A stent crimping apparatus for crimping a deformable radioactive stent onto a deployment device which includes a first jaw member defining a shielded first compression surface, and an opposed, second jaw member defining a shielded second compression surface oriented opposite the first compression surface. The first and second compression surfaces are adapted to collectively form an elongated guide bore formed for axial receipt of the deformable stent and the deployment device therein. To protect against exposure to the radioactive stent, a shield assembly is provided defining an opening into a bore therein which is formed and dimensioned for longitudinal receipt of the deformable stent in an uncrimped condition. A shield assembly defines an opening into the bore, and cooperates with the first and second jaw members to substantially prevent radioactive particles emitted by the radioactive stent from passing out of the crimping apparatus. An operating mechanism is operatively coupled to the first and second jaw members for selective movement between a loading condition and a crimping condition. In the loading condition, the uncrimped stent and the deployment device may be inserted through the opening and into the bore. In the crimping condition, the deformable stent is radially compressed onto the deployment device between the first and second compression surfaces.

31 Claims, 6 Drawing Sheets

STENT CRIMPER APPARATUS WITH RADIATION SHIED

TECHNICAL FIELD

The present invention relates, generally, to intravascular stents and, more particularly, to stent crimping apparatus with radiation shields for radioactive stents.

BACKGROUND ART

Percutaneous Transluminal Angioplasty (PTA) is a medical procedure for widening a stenosis or constriction of a bodily passage. The most common application is to widen the passage of a blood vessel, such as an artery, which has been constricted by the build-up of cholesterol fats or atherosclerotic plaque. When this medical procedure is applied to a coronary artery, it is referred to as Percutaneous Transluminal Coronary Angioplasty (PTCA).

Typically, a tip mounted balloon of a balloon catheter is advanced over a guidewire to the stenosis. Once the balloon catheter is properly positioned, the balloon is inflated to compress the plaque against the vessel walls and widen the stenosis. Problems occur, however, when the dilatation of the occlusion forms fissures, flaps and/or dissections which may ultimately cause reclosure or restenosis of the vessel.

To maintain vessel patency and/or strengthen the area undergoing angioplasty or other treatment, an intravascular prosthesis may be employed. These devices are usually introduced percutaneously, transported transluminally and positioned at a desired location within the widened stenosis of the patient. One form of an intravascular prosthesis is a radially expandable stent device which is typically positioned at the tip of a balloon catheter and is implanted by expansion of the balloon when the balloon and stent device are at the desired location. Expansion of the balloon portion of the catheter can simultaneously compress plaque at that location and expand the stent to its proper implantation size. The balloon portion of the catheter is then deflated and withdrawn from the vessel, leaving the implanted stent as a permanent scaffold to reduce the chance of restenosis.

To adequately mount an unexpanded stent onto the balloon catheter for delivery into the patient, the stent is "crimped" or otherwise radially collapsed sufficiently to attach it to the balloon. One of the most favored crimping techniques is manual crimping performed by the physician in the catheter laboratory. This process enables the physician to "feel" the crimp to determine the crimp quality. The proper crimping of a stent about a balloon catheter, however, is a technique acquired only through practice and can be affected by a variety of subjective conditions. Too much or too little pressure may be applied and the balloon and/or stent may be damaged, lost, or may not otherwise perform as desired during the procedure. In contrast, the physician may not apply sufficient crimping pressure to the stent to load it onto the balloon. During advancement through the vessel or upon deployment, an insufficiently crimped stent may slip or rotate on the catheter during, or in the worst case scenario, come off the balloon catheter entirely; the result of which is not desirable. Moreover, when applying radioactive or radioisotope embedded stents, direct manual handling by physicians and laboratory technicians should be avoided. Such radioisotope embedded stents, for example, are those disclosed in U.S. Pat. Nos.: 5,059,166; 5,176,617; 5,840,009 and 5,871,437, each of which is incorporated by reference in their entirety.

In other instances, the stents may be pre-crimped or preattached onto their associated delivery balloon at the time of production by the manufacturer. While these devices more uniformly control crimping quality, a large inventory of stent-bearing angioplasty catheters must be maintained to accommodate the variety of stent types, diameters and stent lengths for each balloon catheter type. Thus, maintaining such an inventory is not only difficult to store, but can be very expensive as well.

Another technique commonly employed to crimp the stent onto the balloon catheter is through the use of a pair of modified plier-like tools which crimp down on the unexpanded stent. The performance of these tools, however, is not completely satisfactory since there is still a wide divergence between application force, profile and stent diameter. Problems arise when excessive crimping forces are applied to the crimp pliers which can damage the stent and/or balloon catheter. This is especially problemsome given the minute size of the stents which are typically on the order of about one (1) mm to four (4) mm in diameter before crimping. Non-uniformity of the crimping may also be experienced as well as the inability to determine when a reliable and uniform crimp has been achieved. Moreover, these designs are inadequate to handle radioactive or radioisotope embedded stents since they typically cause the physicians and/or laboratory technicians to be subjected to excessive radiation exposure.

DISCLOSURE OF INVENTION

Accordingly, a shielded stent crimping apparatus is provided for crimping a deformable radioactive stent onto a deployment device which includes a first jaw member defining a shielded first compression surface, and an opposed, second jaw member defining a shielded second compression surface oriented opposite the first compression surface. The first and second compression surfaces being adapted to collectively form an elongated guide bore formed for axial receipt of the deformable stent and the deployment device therein. A shield assembly defines an opening into the bore, and cooperates with the first and second jaw members to substantially prevent radioactive particles emitted by the radioactive stent from passing out of the crimping apparatus. An operating mechanism is provided operatively coupled to the first and second jaw members for selective movement between a loading condition and a crimping condition. In the loading condition, the uncrimped stent and the deployment device may be inserted through the opening and into the bore. In the crimping condition, the deformable stent is radially compressed onto the deployment device between the first and second compression surfaces.

The operating mechanism preferably includes a pair of handle members movably coupled to one another for selective operation of the first and second jaw members between the loading condition and the crimping condition. Each handle member includes a proximal portion formed for gripping thereof, and a distal portion coupled to a respective jaw member.

In one embodiment, at least one of the distal portions of the handle members is mounted to a coupling member for pivotal movement between the loading condition and the crimping condition. In another configuration, the operating mechanism further includes a biasing device adapted to bias the jaw members toward the loading condition.

Each of the first and the second compression surfaces preferably defines an elongated compression groove which cooperate to form the guide bore. These grooves further enable aligned compression of the deformable stent onto the deployment device when moved to the crimping condition.

In another aspect of the present invention, the shield assembly includes a proximal end cap portion positioned on one side of the first and second jaw members at proximal end of the bore. The proximal end cap portion is preferably fixedly mounted to the first jaw member for fixed alignment of the opening with the first compression surface. The second jaw member defines a proximal recess portion formed and dimensioned for sliding receipt of the proximal end cap portion therein during movement of the second jaw between the loading condition and the crimping condition. Preferably, the proximal end cap portion and a shoulder portion, defining the proximal recess portion, cooperatively contact in the crimping condition to limit the relative movement of the first jaw member and the second jaw member.

In still another embodiment, a flexible crimp tube is included having a passage dimensioned for longitudinal receipt of the stent therein in the uncrimped condition. The crimp tube includes an outer circumferential dimension formed for longitudinal sliding insertion through the shield assembly opening and into the bore thereof. The crimp tube includes an end fitting configured to interference fit with the shield assembly opening.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

BEST MODE OF CARRYING OUT THE INVENTION

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 1:
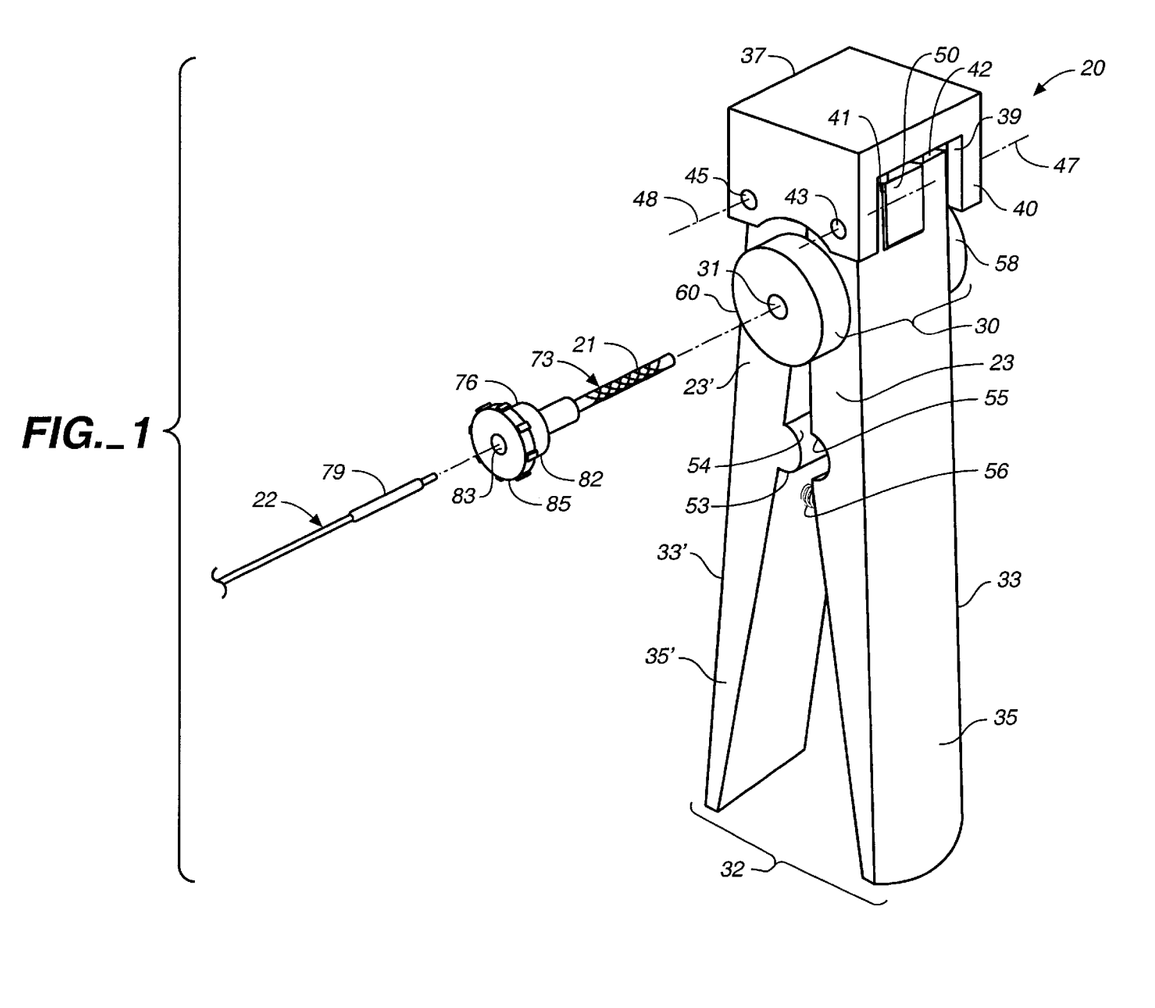
FIG. 1 is a top perspective view of a shielded stent crimping apparatus constructed in accordance with the present invention.
Figure 2A:
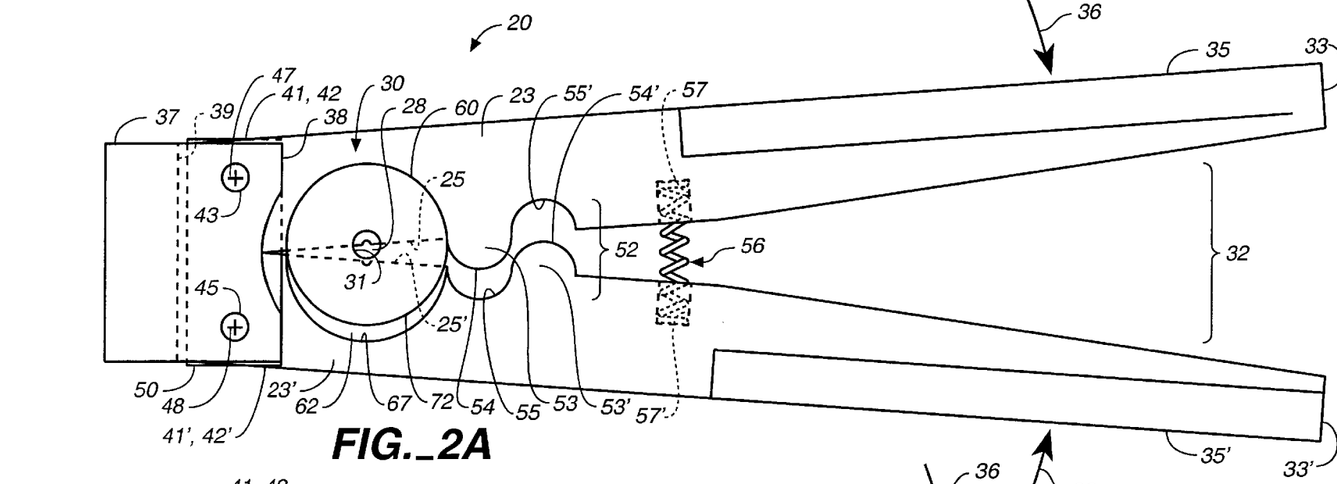
FIGS. 2A and 2B are a series of side elevation views of the stent crimping apparatus, illustrating cooperative from a loading condition to a closed condition.
Figure 2B:
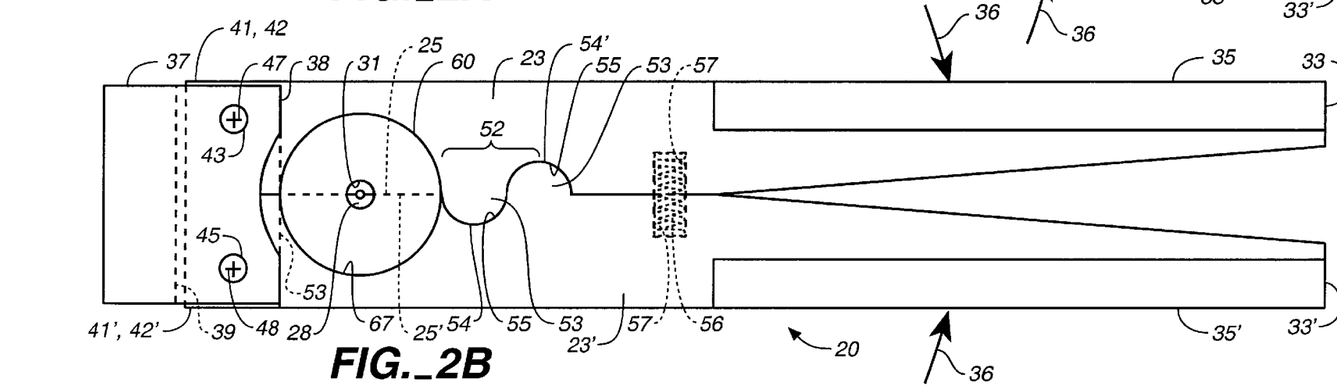
Figure 4A:
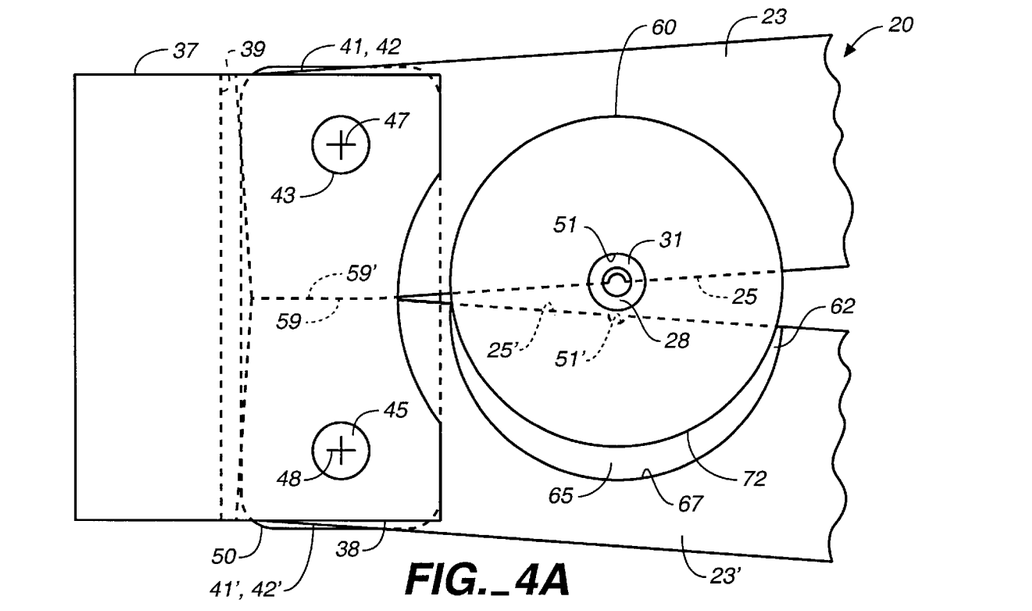
FIGS. 4A and 4B are a series of fragmentary, enlarged, side elevation views, in cross-section, of the stent crimping apparatus of FIGS. 2A and 2B.
Figure 4B:
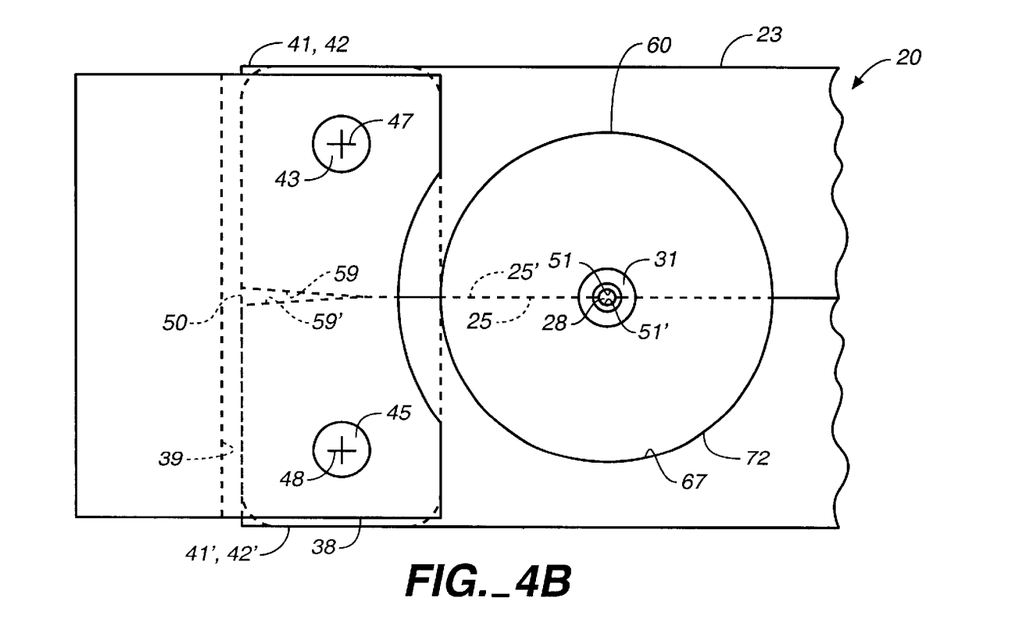
Figure 5A:
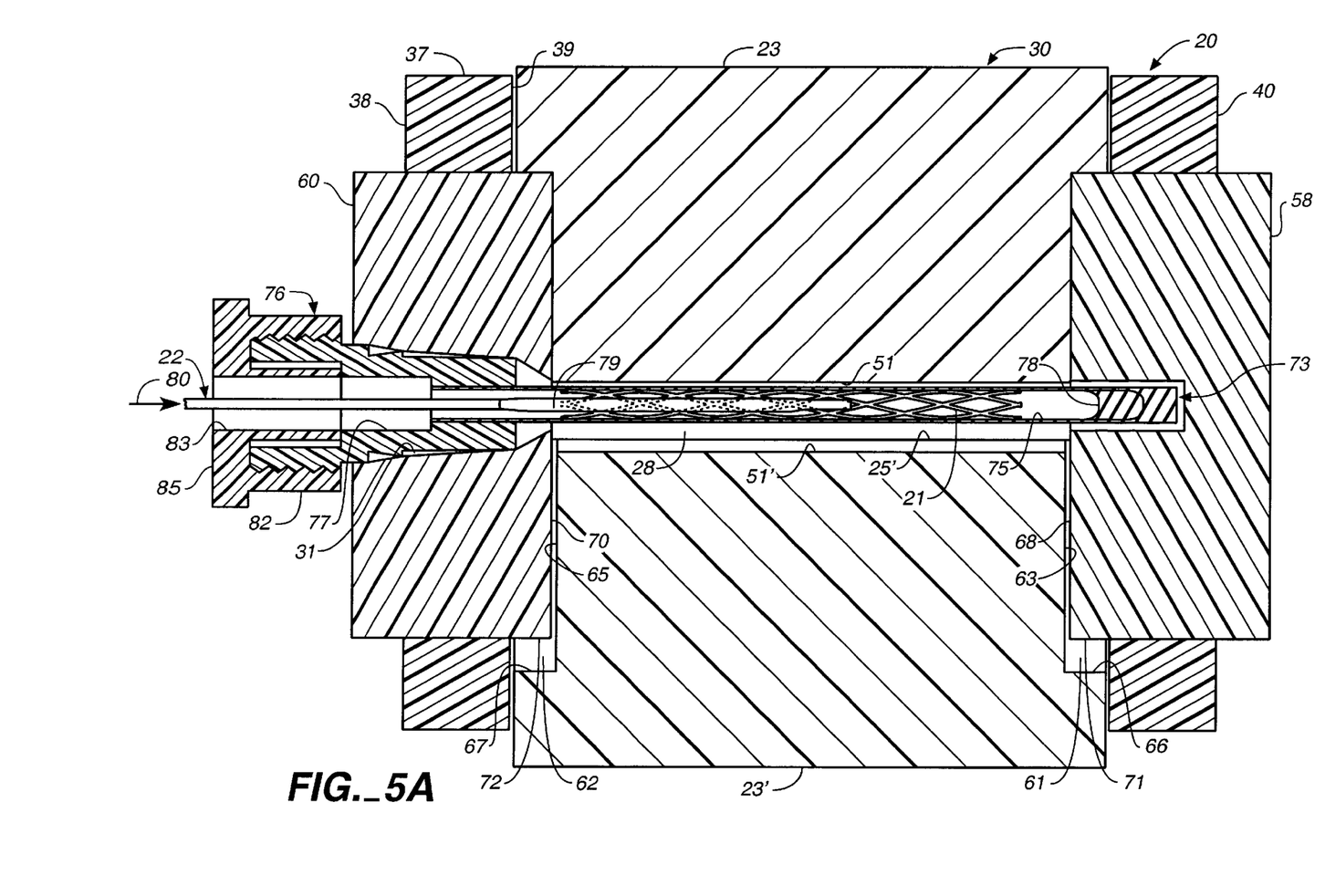
FIGS. 5A and 5B are a series of fragmentary, front elevation views of the stent crimping apparatus taken substantially along the planes of the lines 5—5 in FIGS. 4A and 4B.
Figure 5B:
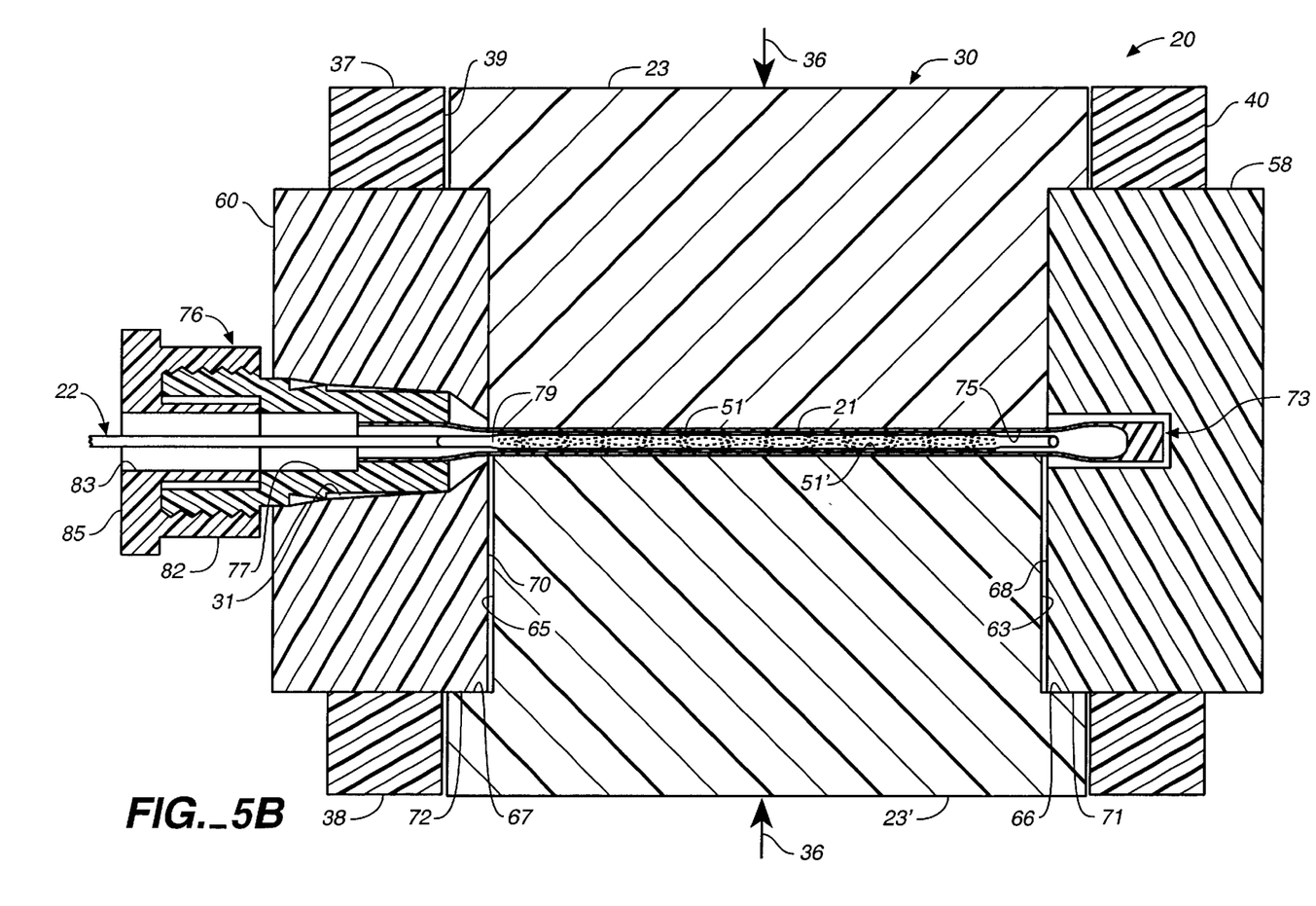

Attention is now directed to FIGS. 1, 2 and 5, where a stent crimping apparatus, generally designated 20, is provided for crimping a deformable radioactive stent 21 onto a deployment device 22. The crimping apparatus 20 includes a first jaw member 23 defining a shielded first compression surface 25, and an opposed, second jaw member 23' defining a shielded second compression surface 25' oriented opposite the first compression surface 25. The first compression surface 25 and the second compression surface 25' are adapted to collectively form an elongated guide bore 28 formed for axial receipt of the deformable stent 21 and the deployment device 22 therein. A shield assembly, generally designated 30, defines an opening 31 into the bore 28, and cooperates with the first and second jaw members 23, 23' to substantially prevent radioactive particles emitted by the radioactive stent 21 from passing out of the crimping apparatus 20. An operating mechanism, generally designated 32, is provided operatively coupled to the first and second jaw members for selective movement between a loading condition (FIGS. 2A, 4A and 5A) and a crimping condition (FIGS. 2B, 4B and 5B). In the loading condition, the uncrimped stent 21 and the deployment device 22 may be inserted through the opening 31 and into the bore 28; while in the crimping condition, the deformable stent 21 is radially compressed onto the deployment device 22 between the first compression surface 25 and second compression surface 25'.

Accordingly, a hand-held stent crimping apparatus is provided for crimping an uncrimped radioactive stent onto a deployment device, such as a balloon catheter, while simultaneously providing sufficient radioactive shielding to the technician during the crimping operation. The opposed jaws are adapted to uniformly distribute the compressive radial forces circumferentially along the stent. Such uniformity of the crimp in the longitudinal direction assures maintenance of the stent on the deployment device, as well as facilitate proper expansion of the stent during deployment.

In the preferred form, the operating mechanism 32 includes a pair of handle members 33, 33' movably coupled to one another for selective operation of the first and second jaw members 23, 23' between the loading condition and the crimping condition. Each elongated handle member 33, 33' includes a respective proximal gripping portion 35, 35' formed for gripping thereof, and an opposed distal portion coupled to the respective jaw members 23, 23'. Preferably, these handle members are integrally formed with the jaw members of the operating mechanism. Hence, as will be described in greater detail below, by manual manipulation of the gripping portions 35, 35', in the direction of arrows 36 in FIG. 2A, the first and second jaw members 23, 23' can be moved from the loading condition to the crimping condition.

Figure 3:
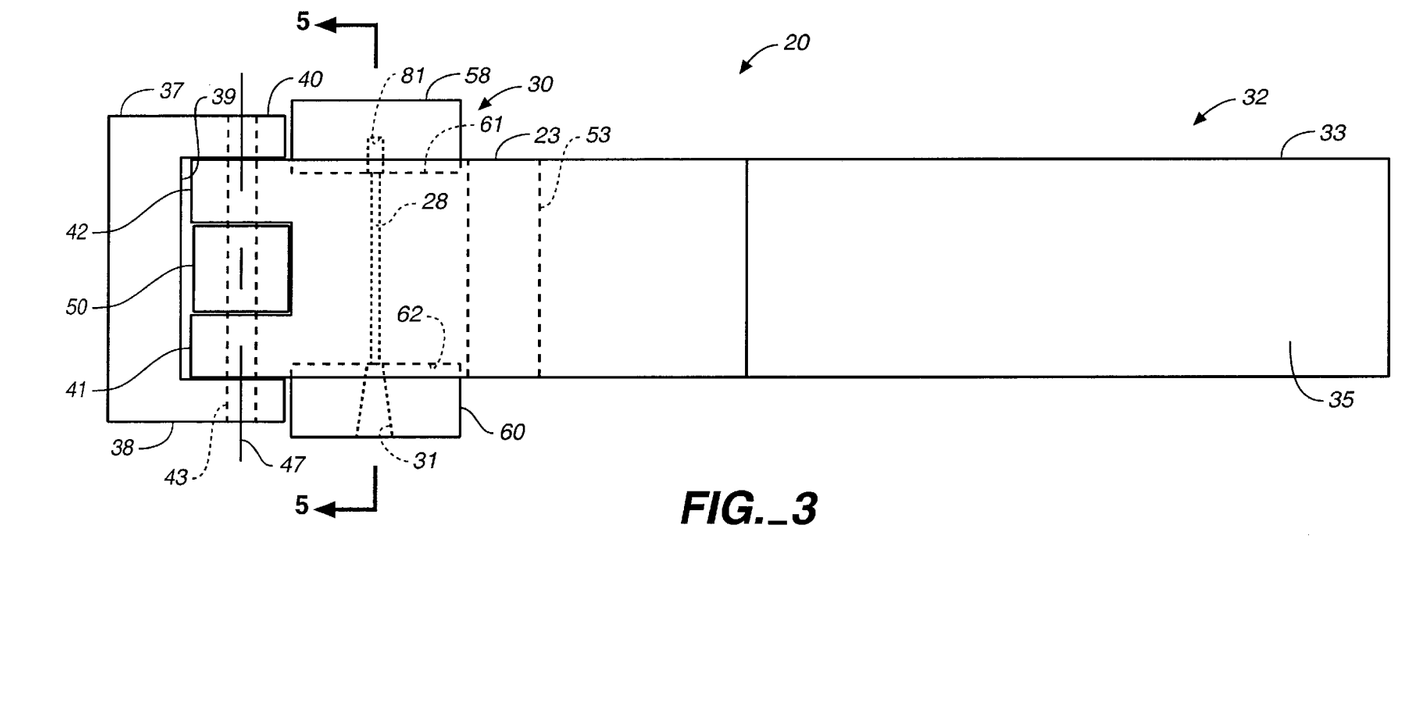
FIG. 3 is a top plan view of the stent crimping apparatus of FIG. 2.

As best viewed in FIGS. 1–3, the crimping apparatus 20 includes a coupling member 37 upon which both the handle members 33, 33' are pivotally secured. The coupling member 37 is preferably U-shaped having a pair of spaced-apart support legs 38 and 40 which define a recess 39 therebetween. Extending distally from each distal portion of the handle members 33, 33' are a pair of spaced-apart ear portions 41, 42 and 41', 42' which are movably mounted to the corresponding support legs 38, 40. To pivotally secure each handle member ear portion 41, 42 and 41', 42' to the corresponding support legs 38, 40 of the coupling member 37, a set of spaced-apart pivot pins 43, 45 are provided extending axially therethrough.

This arrangement, accordingly, enables independent pivotal movement of one handle member 33 about pivot axis 47, and independent pivotal movement of the other handle member 33' about pivot axis 48. To further stabilize the independent movement of the handle member 33, 33', positioned between the respective ear portions 41, 42 and 41', 42' is a stabilizing member 50 which extends between the pivot pins 43, 45. Moreover, by strategically spacing the independent pivotal axis 47, 48 apart and substantially parallel to one another, the first compression surface 25 and the second compression surface 25' can be caused to uniformly radially compress the deformable stent 21 circumferentially therealong when the jaw members move from the loading condition (FIG. 4A) to the crimping condition (FIG. 4B). In contrast, a plier-type configuration would tend to excessively compress the stent 21 at the regions closer to the pivot axis 47, 48 with a greater force than the opposed regions thereof farther from these axes. Consequently, the compressive forces are nonuniform circumferentially about the stent.

FIGS. 4 and 5 best illustrate that each of the first compression surface 25 and the opposed second compression surface 25' form the structure of the first jaw member 23 and the second jaw member 23', respectively, which contact and compress the deformable stent 21. Each compression surface 25, 25' defines an elongated compression groove 51, 51' extending transverse to and across the respective elongated handle members 33, 33'. Preferably, these compression grooves 51, 51' are semi-cylindrical in shape and extend substantially parallel to the pivotal axes 47, 48 of the handle members 33, 33'. Moreover, as shown in FIG. 4, the opening 31 into bore 28 maintains axial alignment with at least one of the compression grooves 51, 51' during compressive displacement of the crimping apparatus. In this manner, upon axial sliding receipt of the deformable stent 21 and deployment device 22 therethrough, the same will be aligned and positioned in between the semi-cylindrical compression grooves 51, 51' for aligned compression thereof.

While the compression grooves 51, 51' extend the full transverse length of each compression surface 25, 25' from one side of the corresponding handle members 33, 33' to the opposite side thereof, the compression grooves 51, 51' must be sufficiently long to accommodate the longitudinal length of deformable stent 21 in the guide bore 28. As viewed in FIG. 5A, the transverse length of the compression surfaces 25, 25' of the corresponding jaw members 23, 23' are therefore slightly longitudinally longer than the length of the deformable stent 21. This assures a continuous and evenly distributed compression of the uncrimped stent 21 from one end to the opposite end thereof.

Collectively, the semi-cylindrical shaped compression grooves 51, 51' cooperate to form the guide bore 28 which is adapted for sliding axial receipt of the deformable stent 21 and the deployment device 22 therein (FIG. 5A). Upon proper positioning of the deformable stent 21 and the deployment device, in the loading condition, the proximal gripping portions 35, 35' of the handle members 33, 33' may be manually manipulated to compress the deformable stent 21 onto the deployment device 22 when moved to the crimping condition (FIG. 5A). As each handle member 33, 33' independently pivots about their respective pivot axis 47, 48, toward the crimping condition, the semi-cylindrical walls defining the compression grooves 51, 51' cooperate to deformably contact the stent for compression thereof. Inward radial compression continues until the opposed compression surfaces 25, 25' of the first jaw member 23 and the second jaw member 23' contact one another (FIGS. 4B and 5B). Due to the geometric arrangement of the independent pivoting handle members 33, 33', when the semi-cylindrical walls of the compression grooves 51, 51' contact the deformable stent, a uniform distribution of compressive radial forces are exterted circumferentially therealong.

As best viewed in FIG. 4B, the opposed semi-cylindrical compression grooves 51, 51' cooperate to determine the maximum degree of compression of the deformable stent onto the deployment device. Hence the diameter of opposed grooves 51, 51' controls the compressed diameter of the stent 21.

In the preferred embodiment, the handle members 33 and 33' are structured to prevent the direct passage of radioisotopes from the guide bore 28 whether in the loading condition or the crimping condition. As best viewed in FIGS. 1, 2A, 2B and 3, to prevent such straight-line passage of the radioisotopes between the first handle member 33 and the second handle member 33', the shield assembly 30 provides a barrier structure in the form of a key member 53 extending substantially adjacent to the compression groove 51 for blocking thereof. The key member 53 is defined by a first mating surface 54 extending across the first jaw member 23 (FIG. 3) and protruding upwardly from the first compression surface 25 by height sufficient to block such straight-line passage. FIGS. 2A and 2B best illustrate that the laterally extending key member 53 is further positioned sufficiently near and adjacent to the guide bore 28, and is sufficiently high to block such straight-line passage.

Positioned opposite the key member 53 is an opposed second mating surface 55 formed and dimensioned for receipt of the key member 53 therein in the crimping condition. Hence, the first mating surface 54 and the second mating surface 55 cooperate in a manner substantially preventing the direct straight-line passage of radioisotopes emitted from the stent radially out of the guide bore 28 of the shield assembly 30 in the direction of the handle members 33, 33' when in the loading condition. To further promote blockage, as viewed in FIGS. 2A and 2B, a second key member 53', positioned opposite to and adjacent the first key member 53, and a second mating recess 55' may be provided. Collectively, the opposed first and second key members cooperate to impair any direct line of site passage of radioisotopes from the bore between the handle members.

To facilitate coaxial alignment of the compression grooves 51, 51' during pivotal movement from the first and second jaw members 23, 23' from the loading condition to the crimping condition, the key member 53 and mating recess 55 further function as an alignment device which cooperates with the handle members 33, 33' to align the first and second compression surfaces 25, 25' (FIGS. 2A and 2B). Such coaxial alignment of the compression grooves is of course necessary to assure that the deformed stent 21 is properly and uniformly compressed onto the deployment device 22.

As mentioned, the key member 53 protrudes outwardly from one of the compression surfaces 25, 25'. The other opposed compression surface 25' defines the mating recess 55 formed and dimensioned for aligned, mating receipt of the key member therein upon pivotal movement of the handle members 33, 33' toward the full crimping condition (FIG. 2B). Accordingly, when the curvilinear surface of the key member 53 seats in the mating curvilinear surface defining the mating recess 55, the opposed compression grooves 51, 51' are coaxially aligned.

It will be appreciated, of course, that the key member 53 and the mating recess 55 need not be cylindrical, but may be some other geometric shape without departing from the true spirit and nature of the present invention. Moreover, the alignment device may further be provided by two or more key member/mating recesses aligned in a series along the compression surfaces 25, 25', as shown in FIGS. 2A and 2B.

To bias the handle members 33, 33', and thus, the jaw members 23, 23' back toward the loading condition from the crimping condition, the operating mechanism 32 preferably includes a biasing device 56. As best illustrated in FIGS. 2 and 4, the biasing device 56 is preferably provided by a compression spring cooperating with the handle members 33, 33', in the crimping condition, to urge the corresponding jaw members 23, 23' toward the loading condition (FIGS. 2A and 4A). In the preferred form, one end of the compression spring 56 is received in receptacle 57 while the opposite end thereof is received in an opposed receptacle 57'.

To limit the pivotal displacement of the handle members 33, 33' in the loading condition (FIGS. 2A and 4A), the distal portions thereof include a pair of contact surfaces, 59, 59'. As best viewed in FIG. 4B, these surfaces are spaced apart in the crimping condition, and then contact one another as the biasing device 56 urges the handle members 33, 33' back toward the loading condition.

Referring back to FIGS. 1, 4 and 5, the shield assembly 30 is preferably integrally formed with the handle members 33, 33' to provide adequate radiation shielding to technicians when the radioactive stent 21 enclosed therein. Hence, as best viewed in FIGS. 5A and 5B, the shield assembly components of the handle members 33, 33' must be of a sufficient radial dimension or diameter to prevent passage of the radioactive particles therethrough. Thus, the necessary thickness of the shield assembly is a function of the shield material and the type of radioisotope emitted from stent. For example, when the components of the shield assembly are formed from a 30% leaded, moldable acrylic and the stent 21 is embedded with a beta particle emitter such as Phosphorus 32 ($^{32}$P), or a low energy gamma emitter such as Palladium 103 ($^{103}$Pd), the diameter of the collective shield assembly 23 should be between about 1.0 inch to about 2.0 inches, and most preferably about 0.5 inch. Other suitable materials, of course, may be employed in whole or in part, such as a polycarbonate, acrylic/polycarbonate with a thin leaded outer shell or a high density metallic material or the like.

In the preferred embodiment, shield assembly 30 includes a pair of end cap portions 58 and 60 positioned on opposite sides of the first and second compression surfaces 25, 25' of the first and second jaw members 23, 23'. These end cap portions 58, 60 are designed to prevent the passage of radiation out of the ends of the guide bore 28 which are emitted from the radioactive stent contained therein. FIGS. 5A and 5B best illustrate that the end cap portions 58, 60 extend sufficiently beyond the corresponding ends of the bore 28 to contain the emitted radiation therein. The far end cap portion 58 is closed off on the end thereof to fully enclose the guide bore, while the near end cap portion 60 defines opening 31 into bore 28. Since these end cap portions 58, 60 provide additional shielding, they should also be of a diameter or thickness sufficient to impede passage of the radioisotopes.

In accordance with the present invention, these end cap portions are fixedly mounted to one of the jaw members 23 or 23' during pivotal operation thereof. As mentioned above, this arrangement enables the opening 31 extending therethrough to be maintained in coaxial alignment with guide bore 28. As the one handle member 33, and the corresponding jaw member 23, move between the loading condition and the crimping condition, the end cap portions 58, 60 likewise move in conjunction therewith to retain their relative position.

The end cap portions 58, 60 are preferably cylindrical shaped having their longitudinal axes coaxially aligned with the guide bore 28. To accommodate these end cap portions 58, 60, when in crimping apparatus is moved to the crimping condition, the side walls of opposed the handle member 33' define a pair of opposed recesses 61, 62 formed for sliding receipt of the corresponding end cap portions 58, 60. As best viewed in FIG. 2A, even when the handle members 33, 33' are oriented in the loading condition, portions of the cylindrical end cap portions 58, 60 are still received in the recesses. This partial receipt is sufficient to contain random radioisotopes which may be passing between the side walls 63, 65 of handle member 33', which define corresponding recesses 61, 62, and the interior walls 68, 70 of the end cap portions 58, 60. When such radioisotopes are passing therethrough, they will ultimately contact a respective restraining wall 66, 67 extending substantially perpendicular to thereto.

Moreover, the restraining walls 66, 67 further perform the function of aligning the opposed compression grooves 51, 51' in a manner similar to the alignment device 52. As the cylindrical end cap portions 58, 60 seat in the recesses 61, 62 when moved from the loading condition (FIG. 5A) to the crimping condition (FIG. 5B), the outer circumferential surface 71, 72 of the end cap portions 58, 60 is formed for aligned contact the opposed restraining walls 66, 67. Since the restraining walls 66, 67 are formed for seated receipt of the corresponding end cap portions 58, 60, these components are strategically positioned to further facilitate alignment between the opposed compression grooves 51, 51'.

In accordance with another aspect of the present invention, a flexibe crimp tube, generally designated 73, is provided to facilitate loading of the uncrimped stent 21 into the bore 28 of the crimping apparatus 20 in the loading condition. As best shown in FIGS. 1, 5A and 5B, the crimp tube 73 provides a passage 75 extending therethrough having an inner diameter dimensioned for longitudinal receipt of the deformable stent 21 therein in an uncrimped form. A proximal end of the crimp tube 73 is coupled to an end fitting 76 having a receiving port 77 in communication with the crimp tube passage 75. The distal end of the crimp tube, however, preferably i includes an end wall 78 to prevent the passage of the deformable stent 21 therethrough. Moreover, when the deployment portion 79 of a deployment device 22, such as a balloon deployment catheter, is advanced through the receiving port 77 and into the tube passage 75 in the direction of arrow 80, as shown in FIG. 5A, the distal end of the deployment catheter 22 may abut the end wall 78 to limit further advancement of the catheter into the crimp tube 73. Preferably, t his abutment facilitates relative positioning and alignment of the deployment portion 79 of the deployment catheter 22 in the uncrimped deformable stent 21 (FIG. 5B).

The outer circumferential dimension of the crimp tube 73 is preferably formed for longitudinal sliding insertion through the opening 31 of the near end cap portion 60 (FIG. 1). When the crimping apparatus 20 is in the loading condition (FIGS. 2A, 4A and 5A), the crimp tube may be advanced into the bore 28 to position the uncrimped stent 21 between the opposed compression grooves 51, 51' of the jaw members 23, 23'. Therefore, the longitudinal length of the crimp tube 73 and passage 75, relative the end fitting 76, are preferably configured to extend in between the opposed compression surfaces 25, 25' and seat the uncrimped stent 21 squarely between the compression grooves 51, 51' of the jaw members 23, 23'. Moreover, the far end cap portion 58 includes a cavity 81 formed for sliding receipt of the distal portion of the crimp tube 73 therein.

In the preferred embodiment, the end fitting 76 is provided by a Touhy-Borst fitting which is configured to interference or snap fit with the near end cap opening 31 to secure the positioning of the crimp tube 73 and the stent 21 between the jaw members 23, 23' (FIG. 5B). Thus, the transverse cross-sectional dimension of the opening 31 is larger than that of the bore 28.

Preferably, a luer lock device 82 of the Touhy-Borst fitting 76 is formed to slideably receive an elongated proboscis portion of any conventional shielded transport mechanism (not shown). These mechanisms, applied in combination with the shield crimping apparatus 20, effectively shield the operator from the radioactive stent or radioactive stent assembly during transport. One such radiation shield, for example, is provided by U.S. Pat. No. 5,605,530 entitled "System for Safe Implantation of Radioisotope Stents" which is incorporated by reference in its entirety. Other such transport devices include U.S. patent application Ser. No. 09/236,770, filed Jan. 25, 1999; and Ser. No. 09/301,442, filed Apr. 28, 1999, all of which are incorporated by reference in their entirety.

The proboscis portion of the radiation shield transport mechanism (not shown) may be slideably inserted into the opening 83 of the luer lock device 82. A nut 85 of the luer lock device 82 may then be operated to form seal around a neck of the proboscis portion. Subsequently, the deployment portion 79 of the deployment catheter 22 is advanced, in the direction of arrow 80, through the receiving port 77 of the Touhy-Borst fitting 76 and into uncrimped stent 21 seated in the passage 75 of the crimp tube 73. During operative movement of the handle members 33, 33' from the loading condition (FIG. 2A) to the crimping condition (FIG. 2B), the jaw members 23, 23' are caused to crimp the stent 21 onto the deployment device 22. The crimped stent and the deployment portion 79 of the deployment catheter 22 may then be retracted from the crimping apparatus and back into the shielded transport mechanism.

In the preferred embodiment, the crimp tube 73 is composed of a relatively flexible material to enable sufficient radial crushing or compression of the deformable stent 21 during the crimping operation. As shown in FIG. 5B, such flexibility accommodates crimping of the deformable stent 21 seated in the crimp tube passage 75. In the preferred form, the thin-walled crimp tube 73 (preferably having a thickness in the range of about 0.005 inch to about 0.012 inch) can be provided by a variety of elastic materials (rubbers, thermoplastics, and thermosets) which include silicon, natural rubber, polyurethane, polyethylene, nylon, polypropylene, polyester, or the like.

What is claimed is:

1. A shielded stent crimping apparatus for crimping a deformable radioactive stent onto a deployment device comprising:

a first jaw member defining a shielded first compression surface;

an opposed, second jaw member defining a shielded second compression surface oriented opposite said first compression surface, said first and second compression surfaces being adapted to collectively form an elongated guide bore formed for axial receipt of said deformable stent and the deployment device therein;

a shield assembly defining an opening into said bore, and cooperating with the first and second jaw members to substantially prevent radioactive particles emitted by the radioactive stent from passing out of said crimping apparatus; and an operating mechanism operatively coupled to said first and second jaw members for selective movement between a loading condition, enabling insertion of the deformable stent and the deployment device through said opening and into said bore, and a crimping condition, radially compressing said deformable stent onto the deployment device between the first and second compression surfaces.

2. The stent crimping apparatus according to claim 1 wherein, said operating mechanism includes a pair of handle members movably coupled to one another for selective operation of said first and second jaw members between the loading condition and the crimping condition.

3. The stent crimping apparatus according to claim 2 wherein, each said handle member includes a proximal portion formed for gripping thereof, and a distal portion coupled to a respective jaw member.

4. The stent crimping apparatus according to claim 3, wherein at least one of said distal portions of said handle members are mounted to a coupling member for pivotal movement between the loading condition and the crimping condition.

5. The stent crimping apparatus according to claim 4, wherein each of said distal portions of the first and second jaw members are pivotally mounted to the coupling member for independent pivotal movement thereof between the loading condition and the crimping condition.

6. The stent crimping apparatus according to claim 5, further including:

an alignment device cooperating with the handle members to align the first and second compression surfaces during pivotal movement of the first and second jaw members from the loading condition to the crimping condition.

7. The stent crimping apparatus according to claim 6, wherein said handle members are pivotally mounted to said coupling member on a distal side of said first and second compression surfaces, and said alignment device cooperatively aligns said handle members on a proximal side of said first and second compression surfaces.

8. The stent crimping apparatus according to claim 4 wherein, each said first and said second compression surface defines an elongated compression groove which cooperate to form the guide bore, and enable aligned compression of the deformable stent onto the deployment device when moved to the crimping condition.

9. The stent crimping apparatus according to claim 8 wherein, each said compression groove is semi-cylindrical.

10. The stent crimping apparatus according to claim 9 wherein, each said compression groove extends transversely across the handle members from one side to an opposite side thereof, and substantially parallel to a pivotal axis of said jaw members.

11. The stent crimping apparatus according to claim 3 wherein, said operating mechanism further includes a biasing device adapted to bias the jaw members toward the loading condition.

12. The stent crimping apparatus according to claim 11 wherein, said biasing device includes a compression spring cooperating with the handle members to urge the jaw members toward the loading condition.

13. The stent crimping apparatus according to claim 3, wherein said shield assembly includes a first mating surface extending across said first jaw member adjacent to said bore, and an opposed second mating surface extending across said second jaw member adjacent to said bore and opposite said first mating surface, said first mating surface and said second mating surface cooperating in a manner substantially preventing the direct straight-line passage of radioisotopes emitted from the stent radially out of the bore of said shield assembly in the direction of said handle members when in the loading condition.

14. The stent crimping apparatus according to claim 13, wherein said first mating surface defines a lip portion extending upwardly from said first compression surface, and said second mating surface defines a recess portion formed and dimensioned for receipt of said lip portion, in the crimping condition.

15. The stent crimping apparatus according to claim 14, wherein each said first and said second compression surface defines an elongated compression groove which cooperate to form the guide bore, and enable aligned compression of the deformable stent onto the deployment device when moved to the crimping condition.

16. The stent crimping apparatus according to claim 14, wherein said opposed mating surfaces are formed and dimensioned to cooperatively align the first and second compression surfaces during movement of the first and second jaw members from the loading condition to the crimping condition.

17. The stent crimping apparatus according to claim 1 wherein, each said first and said second compression surface defines an elongated compression groove which cooperate to form the guide bore, and enable aligned compression of the deformable stent onto the deployment device when moved to the crimping condition.

18. The stent crimping apparatus according to claim 17 wherein, each said compression groove is semi-cylindrical.

19. The stent crimping apparatus according to claim 1 wherein, said shield assembly is integrally formed with said distal portions of said handle members so as to be sufficiently thick radially around said bore to substantially prevent penetration of radioactive particles out of the shield assembly which are emitted from the radioactive stent contained in the bore.

20. The stent crimping apparatus according to claim 1 wherein, said shield assembly includes a proximal end cap portion positioned on one side of said first and second jaw members at proximal end of said bore, said proximal end cap portion defining said opening into said bore.

21. The stent crimping apparatus according to claim 20 wherein, said proximal end cap portion is fixedly mounted to said first jaw member for fixed alignment of said opening with said first compression surface.

22. The stent crimping apparatus according to claim 21 wherein, said second jaw member defines a proximal recess portion formed and dimensioned for sliding receipt of said proximal end cap portion therein during movement of said second jaw between said loading condition and said crimping condition.

23. The stent crimping apparatus according to claim 22 wherein, said shield assembly further includes a distal end cap portion positioned on an opposite side of said first and second jaw members at distal end of said bore.

24. The stent crimping apparatus according to claim 23 wherein, said distal end cap portion is fixedly mounted to said first jaw member, and said second jaw member defines a distal recess portion formed and dimensioned for sliding receipt of said distal end cap portion therein during movement of said second jaw between said loading condition and said crimping condition.

25. The stent crimping apparatus according to claim 21 wherein, said proximal end cap portion and a shoulder portion defining said proximal recess portion cooperatively contact in the crimping condition to limit the relative movement of said first jaw member and said second jaw member.

26. The stent crimping apparatus according to claim 20 further including:

a flexible crimp tube having a passage dimensioned for longitudinal receipt of the stent therein in the uncrimped condition, and an outer circumferential dimension formed for longitudinal sliding insertion through the shield assembly opening and into the bore thereof.

27. The stent crimping apparatus according to claim 26 wherein, said crimp tube includes an end fitting configured to interference fit with the shield assembly opening.

28. The stent crimping apparatus according to claim 27 wherein, the crimp tube passage is formed for sliding receipt of the deployment device through the end fitting and into the stent while in the uncrimped condition.

29. The stent crimping apparatus according to claim 1 further including:

a flexible crimp tube having a passage dimensioned for longitudinal receipt of the stent therein in the uncrimped condition, and an outer circumferential dimension formed for longitudinal sliding insertion through the shield assembly opening and into the bore thereof.

30. The stent crimping apparatus according to claim 29 wherein, said crimp tube includes an end fitting configured to interference fit with the shield assembly opening.

31. The stent crimping apparatus according to claim 30 wherein, the crimp tube passage is formed for sliding receipt of the deployment device through the end fitting and into the stent while in the uncrimped condition.

* * * * *